United States Patent [19]
Strob

[11] Patent Number: 5,559,845
[45] Date of Patent: Sep. 24, 1996

[54] COMPUTED TOMOGRAPHY APPARATUS WITH A ROTATING ANODE X-RAY TUBE AND METHOD FOR OPERATING SAME

[75] Inventor: Wolfgang Strob, Neuendettelsau, Germany

[73] Assignee: Siemens Aktiengesellschaft, Munich, Germany

[21] Appl. No.: 531,278

[22] Filed: Sep. 20, 1995

[30] Foreign Application Priority Data

Dec. 1, 1994 [DE] Germany .................. 44 42 854.5

[51] Int. Cl.⁶ ........................................... A61B 6/03
[52] U.S. Cl. ................................ 378/4; 378/125
[58] Field of Search ..................... 378/4, 125, 135, 378/144

[56] References Cited

U.S. PATENT DOCUMENTS

| | | | |
|---|---|---|---|
| 4,991,189 | 2/1991 | Boomgaarden et al. | 378/4 |
| 5,054,041 | 10/1991 | Hampel | 378/4 |
| 5,090,037 | 2/1992 | Toth et al. | 378/4 |
| 5,224,136 | 6/1993 | Toth et al. | 378/4 |
| 5,335,255 | 8/1994 | Seppi et al. | 378/4 |

*Primary Examiner*—David P. Porta
*Assistant Examiner*—David Vernon Bruce
*Attorney, Agent, or Firm*—Hill, Steadman & Simpson

[57] ABSTRACT

In a computed tomography apparatus having a gantry, on which a rotating anode x-ray tube and a radiation detector are disposed, the gantry being rotatable around a system axis and being tiltable relative to an axis extending perpendicularly to the system axis, the direction of rotation of the gantry is opposite the direction of rotation of the rotating anode in the x-ray tube. Gyroscopic forces acting on the bearing of the rotating anode are thereby at least partially cancelled, significantly reducing mechanical stress on the anode bearing.

2 Claims, 1 Drawing Sheet

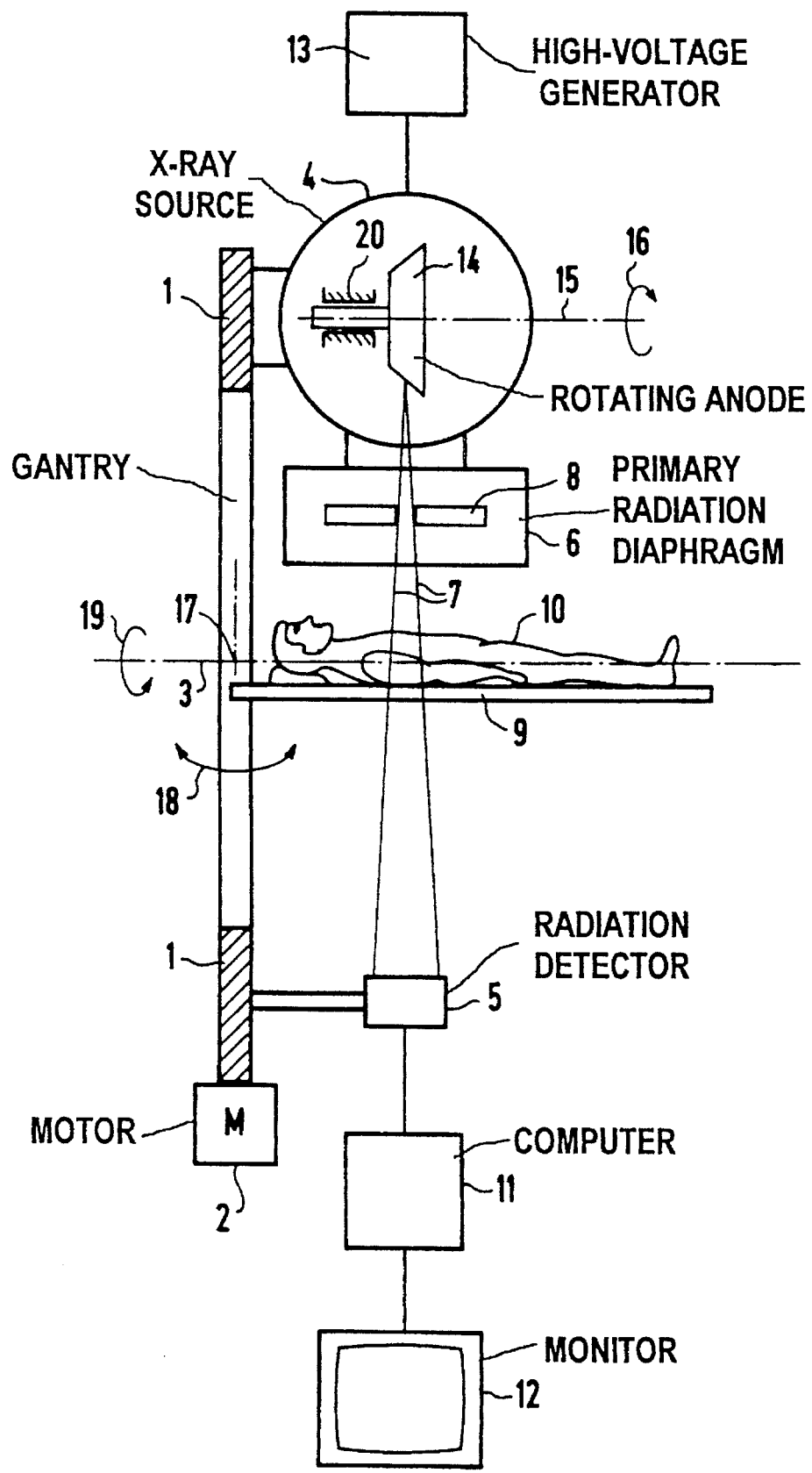

COMPUTED TOMOGRAPHY APPARATUS WITH A ROTATING ANODE X-RAY TUBE AND METHOD FOR OPERATING SAME

BACKGROUND OF THE INVENTION

1. Field of the Invention

The present invention is directed to a computed tomography apparatus and to a method for operating a computed tomography apparatus, and in particular to an apparatus and operating method for a computed tomography apparatus of the type having a rotating anode x-ray tube.

2. Description of the Prior Art

Computed tomography systems are known which employ a rotating anode x-ray tube as the x-ray source. The rotating anode x-ray tube and a radiation detector are disposed opposite each other on a gantry, which is tiltable perperticular system axis, which is parallel to a support on which an examination subject is disposed. The gantry forms a frame on which the x-ray tube and the radiation detector are mounted, and is also rotatable around the system axis for conducting a scan of the examination subject. The gantry is nominally disposed in a plane perpendicular to the system axis, and is tilted out of this plane so that the plane of the scanned slice can be varied (selected).

Because of the rapid rotation of the anode within the x-ray tube, the rotating anode behaves as a gyroscope. When tilting the rotating gantry, gyroscopic moments (force vectors) act on the anode bearing due to the rotation of the anode around its symmetry axis, as well as due to the rotation of the gantry around the system axis. These gyroscopic moments reside perpendicular to a plane defined by the respective rotational axis and the outer tilting moment.

In known computed tomography systems of this type, the rotational direction of the anode and the rotational direction of the gantry are in the same direction. As a result, the gyroscopic forces are cumulative (add together), resulting in a high mechanical stressing of the anode bearing.

SUMMARY OF THE INVENTION

It is an object of the present invention to provide a computed tomography system having a rotating anode x-ray tube as the x-ray source, and having a rotatable, tiltable gantry on which the x-ray source is mounted, wherein stressing of the anode bearing is reduced in comparison to known systems of this type.

The above object is achieved in accordance with the principals of the present invention in a computed tomography system having a rotating anode x-ray tube as the x-ray source, wherein the direction of rotation of the anode and the direction of rotation of the gantry are opposite each other. As a result, the gyroscopic forces which arise due to tilting of the gantry are at least partially cancelled, and the mechanical stress on the anode bearing is therefore reduced in comparison to known systems.

DESCRIPTION OF THE DRAWINGS

The single FIGURE is a schematic side view, partly in section, of a computed tomography apparatus constructed and operating in accordance with the principles of the present invention.

DESCRIPTION OF THE PREFERRED EMBODIMENTS

As shown in the drawing, a computed tomography system for conducting medical examinations has a gantry 1, which is rotated around a system axis 3 by a motor 2. An x-ray source 4 and an x-ray detector 5 are mounted to the gantry 1. The x-ray source 4 is operated to emit a fan-shaped x-ray beam 7, in a fan plane lying perpendicularly to the plane of the drawing. A primary radiation diaphragm 6 is disposed in the path of the fan-shaped x-ray beam 7, for gating the fan-shaped x-ray beam 7 to a desired thickness. The thickness of the fan-shaped x-ray beam 7 is determined by adjustable diaphragm plates 8 in the primary radiation diaphragm 6.

The gated fan-shaped x-ray beam 7 penetrates a measuring field in which a support 9, with a patient 10, disposed thereon, is arranged. The x-ray detector 5, which is composed of a row of individual detector elements, converts the radiation incident thereon, which has been attenuated by the patient 9, into corresponding electrical signals. These electrical signals are supplied to a computer 11, which reconstructs an image of the patient 10 therefrom in a known manner, this image being displayed on a monitor 12.

The x-ray source 4 is supplied by a high voltage generator 13.

Transverse tomograms of selected slices of the patient 10, for example, can be produced using the computed tomography apparatus shown in the drawing. For this purpose, the gantry 1 is rotated through 360° for scanning a selected slice of the patient 10.

The x-ray source 4 is an x-ray tube having a rotating anode 14, which rotates around a rotational axis 15 in a rotational direction indicated by the arrow 16. The rotating anode 14 includes an anode dish attached to a shaft, the shaft being held in a bearing 20, which permits rotation of the shaft therein. Rotation of the rotating anode 14 within the bearing 20 is undertaken in a known manner.

For selecting a position (plane) of the slice of the patient 10 to be examined, the gantry 1 is tiltable relative to an axis 17 extending perpendicularly to the system axis 3. The tilting takes place in the directions indicated by the double arrow 18.

In accordance with the principals of the invention, the direction of rotation of the gantry 1 ensues in the direction indicated by the arrow 19, i.e., counter or opposite to the direction of rotation of the rotating anode 14. As a result, the gyroscopic forces acting on the anode bearing 20 are at least partially cancelled. The anode bearing 20 is thus additionally stressed only to a relatively slight degree upon tilting of the gantry 1.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computed tomography apparatus comprising:

a rotating anode x-ray tube having an anode rotated in a first rotational direction for generating an x-ray beam;

a radiation detector on which said x-ray beam is incident after attenuation of said x-ray beam by an examination subject disposed in said x-ray beam, said radiation detector generating electrical signals corresponding to the x-rays incident thereon;

a tiltable, rotatable gantry on which said rotating anode x-ray tube and said radiation detector are mounted;

means for rotating said gantry in a second rotational direction, opposite to said first rotational direction, for conducting a scan of said examination subject; and means for reconstructing an image of a slice of said examination subject from said electrical signals and for displaying said image.

2. A method for operating a computed tomography apparatus comprising:

generating an x-ray beam from an x-ray tube having a rotating anode disposed therein while rotating said anode in a first rotational direction;

disposing a patient in said x-ray beam;

detecting said x-ray beam, after attenuation thereof by said patient, with an x-ray detector and generating electrical signals corresponding to the attenuated x-ray beam;

rotating said x-ray tube and said x-ray detector around said examination subject, for conducting a scan of said subject, in a second rotational direction, opposite to said first rotational direction; and reconstructing and displaying an image of a slice of said examination subject from said electrical signals.

* * * * *